(12) United States Patent
Slemmen

(10) Patent No.: US 9,492,621 B2
(45) Date of Patent: Nov. 15, 2016

(54) NEEDLE SAFETY DEVICE

(71) Applicant: SANOFI-AVENTIS DEUTSCHLAND GMBH, Frankfurt am Main (DE)

(72) Inventor: John Slemmen, Merseyside (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 103 days.

(21) Appl. No.: 14/349,319

(22) PCT Filed: Oct. 4, 2012

(86) PCT No.: PCT/EP2012/069634
§ 371 (c)(1),
(2) Date: Apr. 2, 2014

(87) PCT Pub. No.: WO2013/050479
PCT Pub. Date: Apr. 11, 2013

(65) Prior Publication Data
US 2014/0288513 A1    Sep. 25, 2014

(30) Foreign Application Priority Data

Oct. 6, 2011  (EP) .................................... 11184103

(51) Int. Cl.
*A61M 5/32* (2006.01)
(52) U.S. Cl.
CPC ............ *A61M 5/3245* (2013.01); *A61M 5/326* (2013.01); *A61M 5/3243* (2013.01); *A61M 5/3257* (2013.01); *A61M 2005/3261* (2013.01); *A61M 2005/3263* (2013.01)
(58) Field of Classification Search
CPC ............ A61M 5/3245; A61M 5/3243; A61M 5/326; A61M 5/3257; A61M 2005/3261
See application file for complete search history.

(56) References Cited

U.S. PATENT DOCUMENTS 4,961,730 A   10/1990   Poncy
5,088,988 A   2/1992   Talonn et al.
(Continued)

FOREIGN PATENT DOCUMENTS

CN   1076371   9/1993
CN   1541124   10/2004
(Continued)

OTHER PUBLICATIONS

International Search Report for Int. App. No. PCT/EP2012/069634, completed Apr. 5, 2013.
(Continued)

*Primary Examiner* — Bradley Osinski
(74) *Attorney, Agent, or Firm* — Fish & Richardson P.C.

(57) ABSTRACT

Described is a needle safety device comprising a needle hub including an axial stem having one or more grooves, a needle having a distal tip, a needle shield telescopically coupled to the needle hub and including a first aperture for allowing the needle to pass through, and an inner sleeve rotatably coupled to the needle shield and including a second aperture for allowing the needle to pass through. The inner sleeve includes one or more resilient arms adapted to engage the groove. In a first axial position and a first angular position, the needle shield covers the distal tip of the needle and the first aperture is aligned with the second aperture. In a second axial position, the distal tip of the needle is through the first aperture and the second aperture and extends distally beyond the needle shield. In a third axial position and a second angular position, the needle shield covers the distal tip of the needle and the first aperture is not aligned with the second aperture.

11 Claims, 5 Drawing Sheets

(56) References Cited

U.S. PATENT DOCUMENTS 5,322,517 A * 6/1994 Sircom ............... A61M 5/3243
 604/198
5,584,810 A 12/1996 Brimhall
5,743,888 A 4/1998 Wilkes et al.

FOREIGN PATENT DOCUMENTS

WO 02/083213 10/2002
WO 2008/035122 3/2008

OTHER PUBLICATIONS

Chinese Office Action in Appl. No. 201280058202.0, dated Jul. 28, 2015, 4 pages.
Chinese Search Report and Written Opinion for Application No. 201280058202.0, Jul. 20, 2015, 2 pages.

* cited by examiner

NEEDLE SAFETY DEVICE

CROSS REFERENCE TO RELATED APPLICATIONS

The present application is a U.S. National Phase Application pursuant to 35 U.S.C. §371 of International Application No. PCT/EP2012/069634 filed Oct. 4, 2012, which claims priority to European Patent Application No. 11184103.7 filed Oct. 6, 2011. The entire disclosure contents of these applications are herewith incorporated by reference into the present application.

TECHNICAL FIELD

This invention relates to a safety needle device that minimizes the risks of accidental needle sticks and provides for needle safety before and after medicament is delivered.

BACKGROUND

Medicament delivery devices (e.g., pen injectors, syringes, auto-injectors, etc.) that contain a selected dosage of a medicament are well known devices for administering the medicament to a patient. Safety devices for covering a needle of the delivery device before and after use are also well known. Typically, a needle shield of the safety device is either manually moved or automatically to surround the medical needle. Various attempts have been made to develop an optimally sized and functioning safety device. However, there remains a need for an optimal safety needle assembly.

SUMMARY

It is an object of the present invention to provide an improved safety needle assembly that minimizes the risk of an accidental needle stick injury, that is safe to handle, and that provides needle safety before and after the medicament is delivered.

In an exemplary embodiment, a needle safety device according to the present invention comprises a needle hub including an axial stem having one or more grooves, a needle having a distal tip, a needle shield telescopically coupled to the needle hub and including a first aperture for allowing the needle to pass through, and an inner sleeve rotatably coupled to the needle shield and including a second aperture for allowing the needle to pass through. The inner sleeve includes one or more resilient arms adapted to engage the groove. In a first axial position and a first angular position, the needle shield covers the distal tip of the needle and the first aperture is aligned with the second aperture. In a second axial position, the distal tip of the needle is through the first aperture and the second aperture and extends distally beyond the needle shield. In a third axial position and a second angular position, the needle shield covers the distal tip of the needle and the first aperture is not aligned with the second aperture.

In an exemplary embodiment, the needle hub includes a proximal ledge adapted to abut a proximal end of the needle shield in the second axial position.

In an exemplary embodiment, the needle hub includes a distal ledge adapted to engage a proximal end of the needle shield.

In an exemplary embodiment, the groove includes a ramped surface. The arm is adapted to follow the ramped surface when the needle shield moves from the second axial position to the third axial position thereby causing rotation of the inner sleeve relative to the needle shield from the first angular position to the second angular position.

In an exemplary embodiment, the needle shield includes a circular flange on an inner surface of a distal face of the needle shield. The inner sleeve includes a ramped ledge on an outer surface of a distal face, wherein the ramped ledge is adapted to engage the flange.

In an exemplary embodiment, the needle shield includes one or more retention snaps adapted to engage the inner sleeve to prevent axial displacement of the inner sleeve relative to the needle shield.

In an exemplary embodiment, the needle shield includes one or more ratchet pawls adapted to engage a ratchet surface on the inner sleeve in the second angular position.

In an exemplary embodiment, the needle safety device further comprises a spring element disposed between the needle hub and the inner sleeve. The spring element applies a distally directed force to the inner sleeve in the second axial position.

In an exemplary embodiment, the inner sleeve is arranged eccentrically relative to an axis A of the needle shield.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
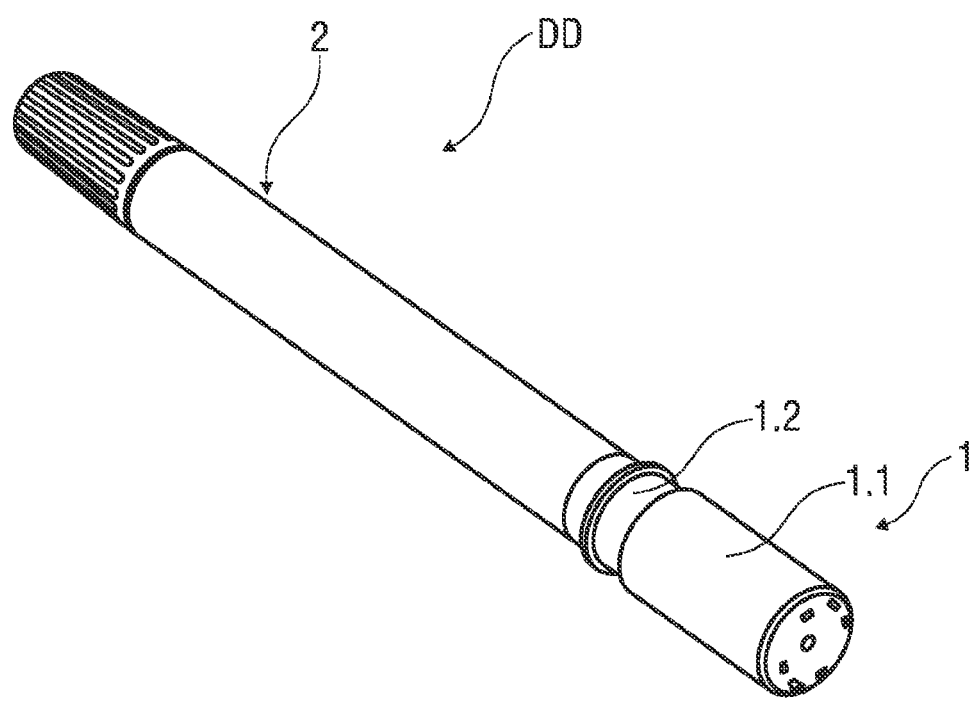
FIG. 1 shows a perspective view of an exemplary embodiment of a medicament delivery device and a needle safety assembly.

FIG. 1 shows a perspective view of an exemplary embodiment of a medicament delivery device DD for administering a medicament to a patient and a needle safety device 1. The delivery device DD may be arranged as a syringe, a dental syringe, an auto-injector, a pen injector or a similar device suitable for delivering a medicament. In an exemplary embodiment shown, the delivery device DD includes an elongate housing 2 which contains a container of the medicament. The needle safety device 1 may be removably coupled to the housing 2 or integrally formed with the housing 2. In an exemplary embodiment, the needle safety device 1 comprises a needle shield 1.1, a needle hub 1.2 and a needle 1.3.

Figure 2:
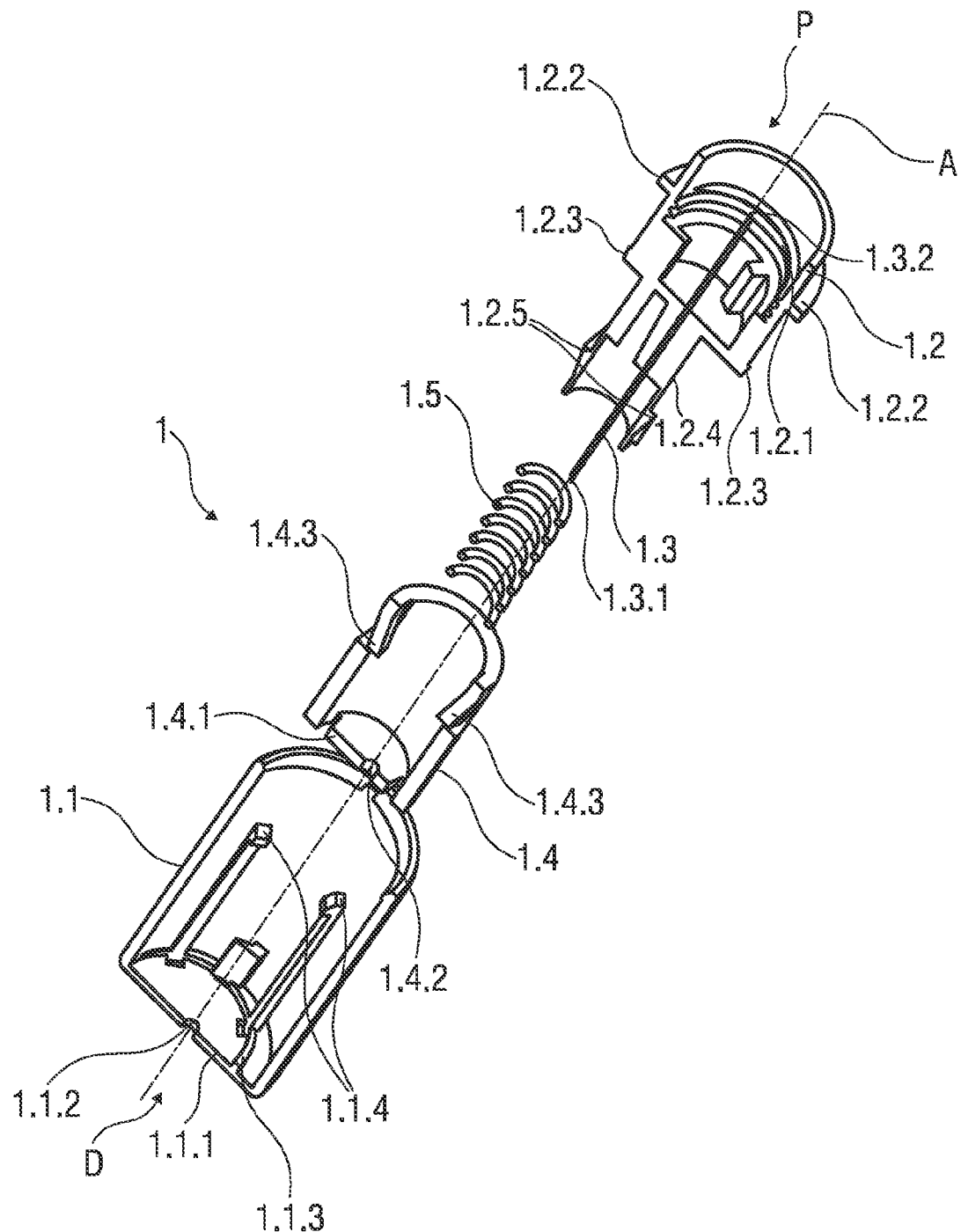
FIG. 2 shows a sectional and exploded view of an exemplary embodiment of a needle safety device.

FIG. 2 shows a sectional and explosion view of an exemplary embodiment of a needle safety device 1 according to the present invention. The needle shield 1.1 is telescopically coupled to the needle hub 1.2 so as to cover and expose a distal tip 1.3.1 of the needle 1.3. The needle shield 1.1 is concentrically arranged about an axis A defined by the needle 1.3. A distal face 1.1.1 of the needle shield 1.1 includes a first aperture 1.1.2 concentrically aligned with the axis A and the needle 1.3 and is adapted to allow the needle 1.3 to pass through during an injection procedure. For example, during use of the needle safety device 1, the needle shield 1.1 may be axially translated relative to the needle hub 1.2 in a proximal direction P so that the distal tip 1.3.1 of the needle 1.3 projects from the needle shield 1.1 in a distal direction D.

In an exemplary embodiment, an inner sleeve 1.4 is rotatably arranged within the needle shield 1.1 and eccentrically arranged with respect to the axis A (e.g., an axis of the inner sleeve 1.4 is parallel to but radially offset from the axis A of the needle shield 1.1). The inner sleeve 1.4 has a distal face 1.4.1 with a second aperture 1.4.2 adapted to allow the distal tip 1.3.1 of the needle 1.3 to pass through. The second aperture 1.4.2 may be eccentrically arranged on the distal face 1.4.1 in a manner that allows the medical needle 1.3 to protrude through the first and second apertures 1.1.2, 1.4.2 when aligned. In an exemplary embodiment, before and during use of the needle safety device 1, the first and second apertures 1.1.2, 1.4.2 are aligned allowing for a passage of the needle 1.3.

In an exemplary embodiment, a circular flange 1.1.3 is eccentrically arranged on an inner surface of the distal face 1.1.3 of the needle shield 1.1. The inner sleeve 1.4 may include a ramped ledge formed on the distal face 1.4.1 adapted to cooperate with the circular flange 1.1.3.

In an exemplary embodiment, a plurality of retention snaps 1.1.4 protrude radially inwards from an inner surface of the needle shield 1.1. The retention snaps 1.1.4 are adapted to abut a proximal end of the inner sleeve 1.4 to prevent axial displacement of the inner sleeve 1.4 relative to the needle shield 1.1. The circular flange 1.1.3 and the retention snaps 1.1.4 mount the inner sleeve 1.4 to the needle shield 1.1 in a manner that allows for a rotation of the inner sleeve 1.4 within the needle shield 1.1 and prevents axial displacement of the inner sleeve 1.4 relative to the needle shield 1.1.

In the exemplary embodiment shown in FIG. 2, the needle 1.3 is arranged as a double pointed needle with a pointed distal tip 1.3.1 and a pointed proximal tip 1.3.2. The pointed proximal tip 1.3.2 is adapted to be inserted into a container of medicament in the delivery device DD when the needle safety device 1 is coupled to the delivery device DD.

In an exemplary embodiment, the needle hub 1.2 comprises a thread 1.2.1 for mating with a corresponding thread on the delivery device DD. In other exemplary embodiments, the needle hub 1.2 may be attached to the delivery device DD by other suitable couplings, like for example bayonet type couplings, snap-fit couplings, frictional couplings or luer type couplings.

The needle hub 1.2 may further comprise a proximal ledge 1.2.2 and a distal ledge 1.2.3 which form bearing surfaces for the needle shield 1.1 allowing an axial translation of the needle shield 1.1 with respect to the needle hub 1.2 between these ledges 1.2.2, 1.2.3. The distal ledge 1.2.3 may include hooks adapted to abut corresponding hooks formed on a proximal end of the needle shield 1.1. The hooked engagement may prevent the needle shield 1.1 from being removed from the needle hub 2.2 in a distal direction. The proximal ledge 1.2.2 may abut the proximal end of the needle shield 1.1, acting as a stop member to prevent further proximal movement of the needle shield 1.1 relative to the needle hub 1.2.

In an exemplary embodiment, the needle hub 1.2 includes a stem 1.2.4 which is adapted to telescopically engage the inner sleeve 1.4. The inner sleeve 1.4 is rotatable relative to the stem 1.2.4. The stem 1.2.4 may include one or more grooves 1.2.5 having a ramped surface 1.2.5.1 disposed at an angle relative to the axis A.

The inner sleeve 1.4 comprises at least one resilient arm 1.4.3 adapted to engage the groove 1.2.5. The arm 1.4.3 may be, in an non-deflected position, oriented toward a longitudinal axis of the inner sleeve 1.4. When the arm 1.4.3 abuts the stem 1.2.4, the arm 1.4.3 may deflect radially until it engages the groove 1.2.5 and abuts the ramped surface 1.2.5.1.

The needle safety device 1 further comprises a spring element 1.5 that is adapted to bias the inner sleeve 1.4 and the needle shield 1.1 in the distal direction D relative to the needle hub 1.2. In an exemplary embodiment, the spring element 1.5 is arranged within the inner sleeve 1.4 bearing proximally against the stem 1.2.4 and distally on an inner surface of the distal face 1.4.1 of the inner sleeve 1.4. In an exemplary embodiment, the spring element 1.5 may be arranged in an unstressed state. In another exemplary embodiment, the spring element 1.5 is arranged in a pre-stressed state. The spring element 1.5 is compressed and energized during use of the needle safety device 1 by translating the needle shield 1.1 relative to the needle hub 1.2 in the proximal direction P.

Figure 3:
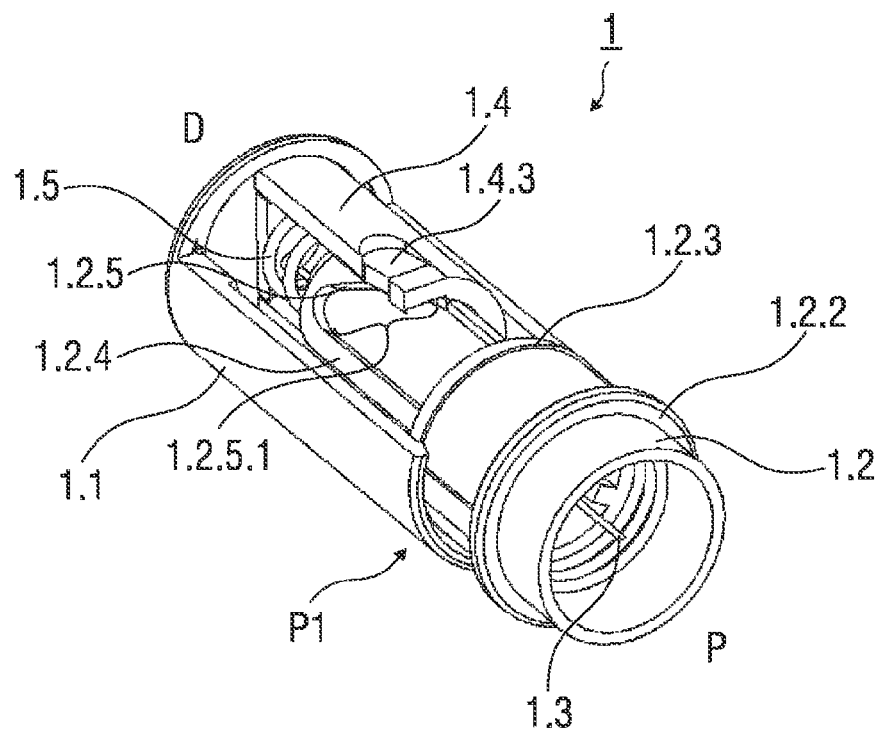
FIGS. 3 and 4 show perspective views of an exemplary embodiment of a needle safety device before use.
Figure 4:
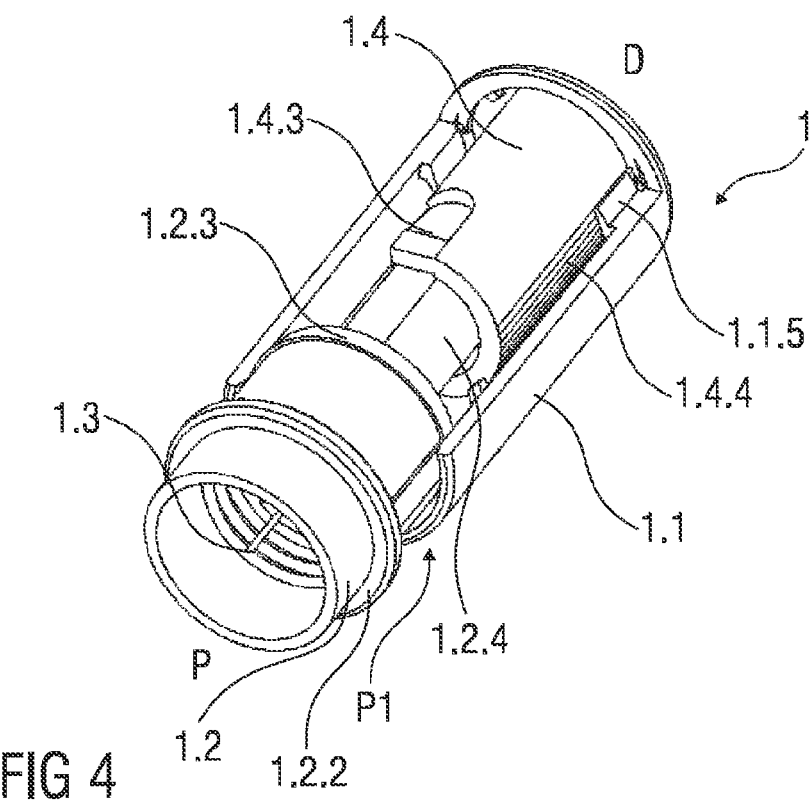

FIGS. 3 and 4 show perspective views of an exemplary embodiment of the needle safety device 1 with partly cut-away portions for viewing internal parts in more detail.

Figure 5:
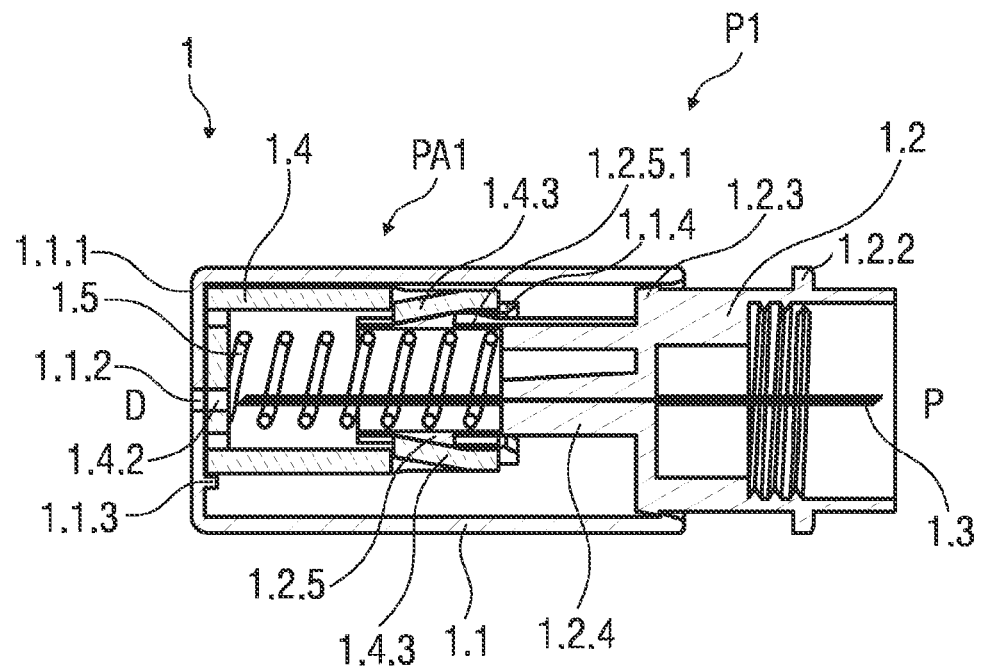
FIG. 5 shows a sectional view of an exemplary embodiment of a needle safety device before use.

FIGS. 3, 4 and 5 show the needle safety device 1 in which the needle shield 1.1 is in a first axial position (PA1) relative to the needle hub 1.2, and the inner sleeve 1.4 is in a first angular position (P1) relative to the needle shield 1.1. In the first axial position (PA1), the needle shield 1.1 covers the distal tip 1.3.1 of the needle 1.3. As can be seen in FIG. 3, in the first axial position (PA1) and the first angular position (P1), the arm 1.4.3 of the inner sleeve 1.4 may be deflected radially by the stem 1.2.4.

Figure 6:
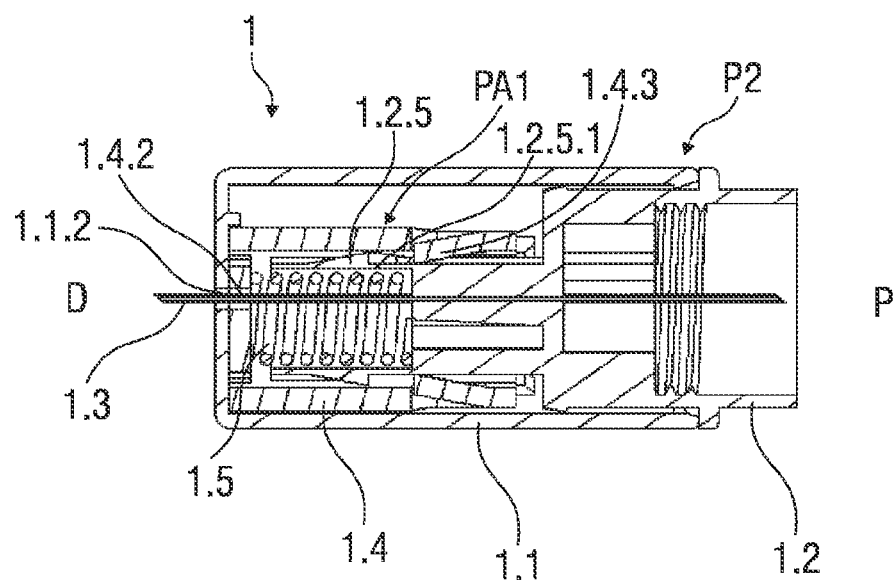
FIG. 6 shows a sectional view of an exemplary embodiment of a needle safety device during use.

Upon an axial translation of the needle shield 1.1 with respect to the needle hub 1.2 from the first axial position (PA1) to a second axial position (PA2), which is shown in FIG. 6, in the proximal direction P, when the arm 1.4.3 reaches the groove 1.2.5, the arm 1.4.3 returns to its non-deflected position and engages the groove 1.2.5. When the arm 1.4.3 has engaged the groove 1.2.5, the arm 1.2.5 may abut the ramped surface 1.2.5.1.

Figure 7:
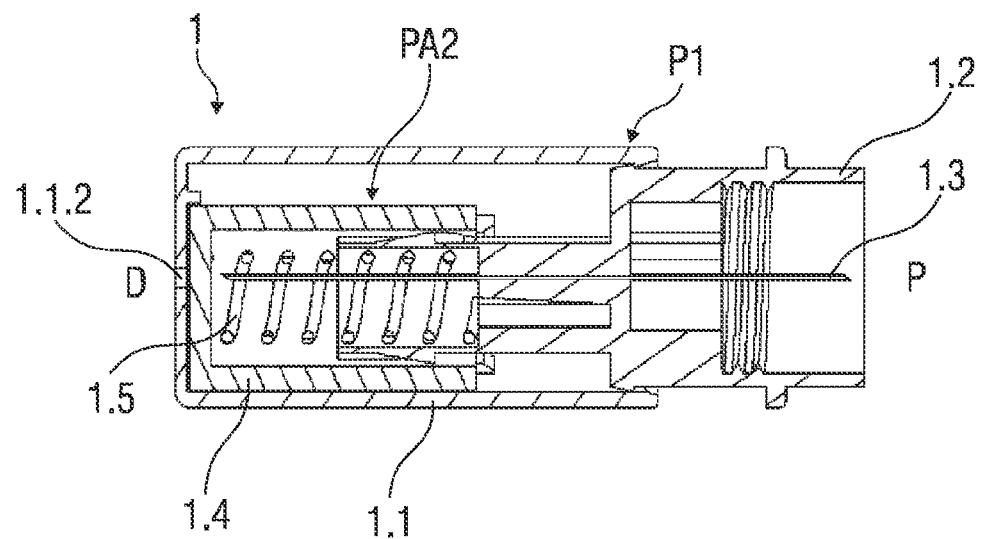
FIG. 7 shows a sectional view of an exemplary embodiment of a needle safety device after use.

Upon an axial translation of the needle shield 1.1 with respect to the needle hub 1.2 (e.g., under the force of the spring element 1.5) from the second axial position (PA2) to a third axial position (PA3), shown in FIG. 7, the arm 1.2.5 follows along the ramped surface 1.2.5.1 causing the inner sleeve 1.4 to rotate to a second angular position (P2) relative to the needle shield 1.1 as the needle shield 1.1 moves in the distal direction D. Rotation of the inner sleeve 1.4 is also guided by the engagement of the ramped ledge on the distal face 1.4.1 of the inner sleeve 1.4 and the circular flange 1.1.3 on the needle shield 1.1.

Due to the rotation of the inner sleeve 1.4 relative to the needle shield 1.1 from the first angular position (P1) to the second angular position (P2) and the axial translation of the needle shield 1.1 with respect to the needle hub 1.2 from the second axial position (PA2) to the third axial position (PA3), the needle 1.3 is covered by the needle shield 1.1 and the first and second apertures 1.1.2, 1.4.2 become misaligned in such a manner that the needle 1.3 can no longer pass through the apertures 1.1.2, 1.4.2.

In the third axial position (PA3), the needle shield 1.1 and the inner sleeve 1.4 may locked and secured in such a way that a return movement to the first angular position (P1) is prevented. In an exemplary embodiment, an inner surface of the needle shield 1.1 may be provided with at least one ratchet pawl 1.1.5 which is adapted to engage a ratchet surface 1.4.4 formed on outer surface of the inner sleeve 1.4 when the inner sleeve 1.4 rotates from the first angular position (P1) to the second angular position (P2).

Therefore, in the third axial position (PA3) and the second angular position (P2), the needle safety device 1 is needle-safe, because the distal tip 1.3.1 of the needle 1.3 can no longer be exposed. Due to misalignment of the first and second apertures 1.1.2, 1.4.2, any attempted proximal movement of the needle shield 1.1 relative to the needle hub 1.2 will cause the distal face 1.4.1 of the inner sleeve 1.4 to abut the distal tip 1.3.1 of the needle 1.3.

In an exemplary embodiment, a removable film may be disposed on the distal face 1.1.1 of the needle shield 1.1, e.g., to maintain sterility of the needle 2.3.

The needle safety device 1 may improve needle safety and in particular minimize the risk that a used needle 1.3 is exposed, so that a transmission of blood-borne diseases, like for example HIV, AIDS, Hepatitis B or Hepatitis C may be avoided.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle safety device, comprising:
    a needle hub including an axial stem having one or more grooves;
    a needle having a distal tip;
    a needle shield telescopically coupled to the needle hub, the needle shield including a first aperture for allowing the needle to pass through; and
    an inner sleeve rotatably coupled to the needle shield and including a second aperture for allowing the needle to pass through, the inner sleeve including one or more resilient arms adapted to engage the one or more grooves,
    wherein, in a first axial position and a first angular position, the needle shield covers the distal tip of the needle and the first aperture is aligned with the second aperture,
    wherein, in a second axial position, the distal tip of the needle is through the first aperture and the second aperture and extends distally beyond the needle shield, and
    wherein, in a third axial position and a second angular position, the needle shield covers the distal tip of the needle and the first aperture is not aligned with the second aperture.

2. The needle safety device according to claim 1, wherein the needle hub includes a proximal ledge adapted to abut a proximal end of the needle shield in the second axial position.

3. The needle safety device according to claim 1, wherein the needle hub includes a distal ledge adapted to engage a proximal end of the needle shield.

4. The needle safety device according to claim 1, wherein the one or more grooves, includes a ramped surface.

5. The needle safety device according to claim 4, wherein the one or more resilient arms is adapted to follow the ramped surface when the needle shield moves from the second axial position to the third axial position thereby causing rotation of the inner sleeve relative to the needle shield from the first angular position to the second angular position.

6. The needle safety device according to claim 1, wherein the needle shield includes a circular flange on an inner surface of a distal face of the needle shield.

7. The needle safety device according to claim 6, wherein the inner sleeve includes a ramped ledge on an outer surface of a distal face of the inner sleeve, wherein the ramped ledge is adapted to engage the flange.

8. The needle safety device according to claim 1, wherein the needle shield includes one or more retention snaps adapted to engage the inner sleeve to prevent axial displacement of the inner sleeve relative to the needle shield.

9. The needle safety device according to claim 1, wherein the needle shield includes one or more ratchet pawls adapted to engage a ratchet surface on the inner sleeve in the second angular position.

10. The needle safety device according to claim 1, further comprising:
    a spring element disposed between the needle hub and the inner sleeve, the spring element applying a distally directed force to the inner sleeve in the second axial position.

11. The needle safety device to claim 1, wherein the inner sleeve is arranged eccentrically relative to an axis A of the needle shield.

* * * * *